United States Patent [19]

Leason

[11] Patent Number: 4,547,190
[45] Date of Patent: Oct. 15, 1985

[54] INLET BLOOD FILTER ASSEMBLY
[75] Inventor: Hayden L. Leason, Humacao, P.R.
[73] Assignee: Filtertek, Inc., Hebron, Ill.
[21] Appl. No.: 444,840
[22] Filed: Nov. 26, 1982
[51] Int. Cl.$^4$ ............................................. A61M 5/14
[52] U.S. Cl. ..................................... 604/185; 604/252
[58] Field of Search ........................ 604/185, 251–255
[56] References Cited

U.S. PATENT DOCUMENTS

| 3,003,500 | 10/1961 | Barton et al. | 604/185 |
| 3,021,841 | 2/1962 | Burke | 604/185 |
| 3,035,575 | 5/1962 | Broman | 604/185 |
| 3,542,026 | 11/1970 | Bledsoe | 604/185 |
| 4,038,983 | 8/1977 | Mittleman et al. | 604/185 X |

Primary Examiner—Dalton L. Truluck
Attorney, Agent, or Firm—Willian, Brinks, Olds, Hofer, Gilson & Lione Ltd.

[57] ABSTRACT

The present invention relates to an inlet blood filter assembly. The inlet blood filter assembly includes a drip chamber, filter chamber and pump chamber. The assembly is constructed so that blood flows through the drip chamber, into the filter chamber and into the pump chamber. The inlet blood filter assembly is blow molded so that the thickness of the walls of the chambers may be varied.

9 Claims, 1 Drawing Figure

U.S. Patent    Oct. 15, 1985    4,547,190
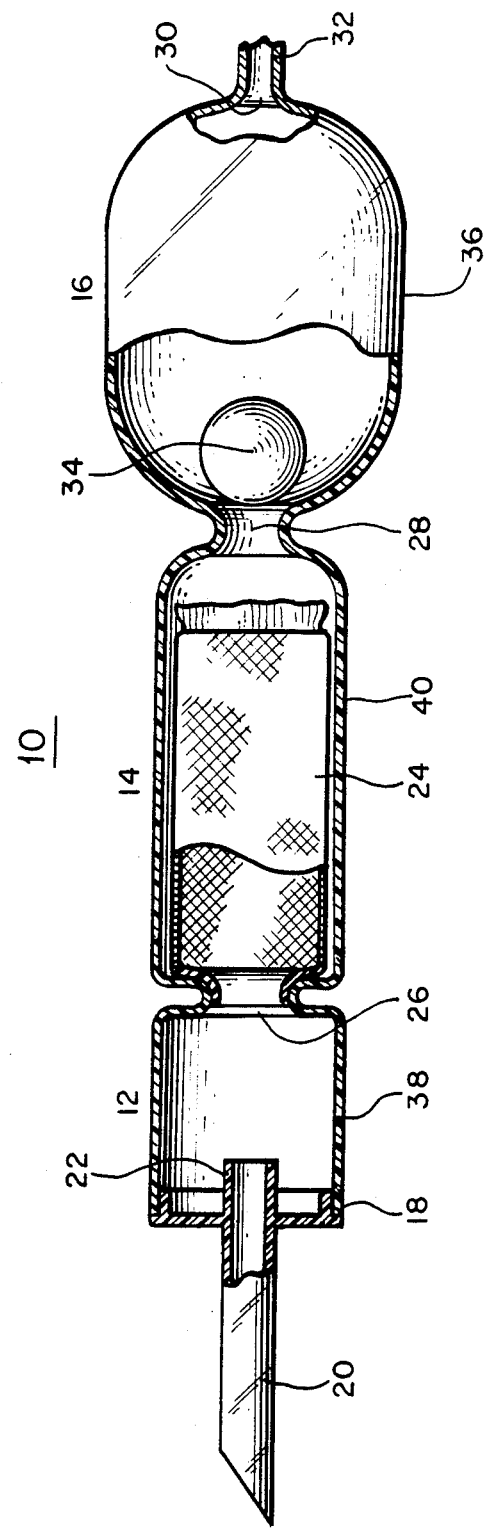

INLET BLOOD FILTER ASSEMBLY

BACKGROUND OF THE INVENTION

This invention relates generally to fluid administration sets and specifically to inlet blood filter assemblies. Inlet blood filter assemblies are used in the administration of blood into a patient. These assemblies function as the inlet end of various blood, and other fluid administration sets.

Typical inlet assemblies include a spike, drip chamber, pump chamber and filter member. The flow of fluid or blood is from the spike, through the drip chamber and pump chamber and then into the filter chamber. In the filter chamber large particulate is removed. The filter chamber is especially important when blood is being administered as whole blood tends to coagulate and therefore contains clots which must be filtered out. After the fluid has been filtered it exits the inlet filter assembly and enters an administration set tubing where it is administered into a patient.

Inlet blood filter assemblies are equipped with a pump chamber so that the flow rate of the fluid through the inlet filter assembly may be increased. Typically, it is necessary to administer fluid faster than the normal gravity pressure. This is especially true in trauma patients who have experienced great losses of blood. These pump chambers are especially useful in view of the fact that whole blood is stored in a cold environment thus decreasing its fluid flow rate. By compressing the pump chamber the fluid is forced through the inlet blood filter assembly.

In spite of the need to increase the fluid flow rate in trauma patients the use of the pump chamber suffers a major drawback. Because the pump chamber is located above (upstream from) the filter chamber, the utilization of the pump chamber to increase the fluid flow rate, sacrifices the efficiency of the filter. The efficiency of a filter is inversely proportional to the fluid pressure of the fluid to be filtered. When the pump chamber is compressed small clots of blood are forced through the filter into the patient. There has therefore been an unsolved need for an inlet blood filter assembly construction wherein the compression of the pump chamber did not sacrifice the filters efficiency.

Typically, these inlet blood filter assemblies are constructed from a straight piece of extruded tubing which is deformed through RF heating and pressure around the various other component pieces to form sealed joints and/or chambers. These joints and chambers are usually done one at a time and in some cases require the addition of a filler sleeve to obtain a suitable bond. Because of this construction these inlet blood filter assemblies are of a uniform thickness, i.e., the walls of the drip and pump chambers have the same thickness.

Because a very necessary feature of the pump chamber is flexibility it is desirous to create a pump chamber with thin walls. Due to the fact that these assemblies are typically a straight piece of extruded tubing the thinning of the walls of the pump chamber would also thin the walls of the remaining portions of the inlet blood filter assembly. This has thus prohibited an inlet blood filter with a pump chamber with thin walls. Thus, there has been an unsolved need for an inlet blood filter assembly unit with a flexible thin walled pump chamber.

SUMMARY OF THE INVENTION

The inlet blood filter assembly of this invention includes a drip chamber, filter chamber and pump chamber. The chambers are arranged so that blood or other fluid flows through the drip chamber into the filter chamber and into the pump chamber. The pump chamber includes a ball-check so that when the chamber is compressed fluid will not be forced into the filter chamber.

The inlet blood filter assembly is created through blow molding so that the wall thickness of the pump chamber may be varied with respect to the remaining portions of the filter assembly. This process also creates an integral filter assembly unit.

Accordingly, an advantage of the present invention is to provide an inlet blood filter assembly wherein the blood is filtered before entering the pump chamber.

A further advantage of the invention is to provide an inlet blood filter assembly which has varied wall thickness.

Another advantage of the present invention is to provide a pump chamber in an inlet blood filter unit which has wall members which are of a thickness which is less than the remaining wall members of the assembly.

A further advantage of the invention is to provide a more efficient inlet blood filter assembly.

Additional features and advantages are described in, and will become apparent from, the detailed description of the preferred embodiments and the drawings.

BRIEF DESCRIPTION OF THE DRAWING

The FIGURE is a perspective view with parts broken away of a preferred embodiment of the inlet blood filter assembly of the present invention.

DETAILED DESCRIPTION OF THE INVENTION

The FIGURE shows the inlet blood filter assembly 10 of the present invention. The inlet blood filter assembly 10 includes a drip chamber 12, a filter chamber 14 and pump chamber 16. The three chambers are arranged so that blood first enters the drip chamber 12 and then passes through the filter chamber 14 and then enters the pump chamber 16, as will be described below. Preferably the inlet blood filter assembly 10 is made from vinyl.

Blood or other fluid enters the inlet blood filter assembly 10 at the drip chamber 12. Connected to a top end 18 of the drip chamber 12 is a spike 20. The spike 20 is sealed to the top 18 of the drip chamber 12 by solvent bonding or in some other fashion. The spike 20 is constructed so that it will pierce a plasma bag or tubing and allow fluid to flow from the plasma bag or tubing through the spike 20 into the drip chamber 12.

The spike 20 includes a drop former 22 from which the blood exits the spike and enters the drip chamber 12. The drop former 22 allows blood to enter the drip chamber 12 at a controlled rate. To this end, as the blood exits the spike 20 through the drop former 22, the user of the inlet blood filter assembly 10 is able to count the drops of blood and determine the fluid flow rate of the blood into the filter assembly 10.

In fluid communication with the drip chamber 12 is the filter chamber 14 which includes a filter screen member 24. The filter screen member 24 is tubular in shape extending for substantially the entire length of the filter chamber 14. To this end, the filter screen member 24 is bonded within the opening 26 of the filter chamber 14 through heat or radio waves, so that fluid which flows from the spike 20 through the drip chamber 12 must enter the filter screen member 24 as it flows through the inlet blood filter assembly 10.

The filter screen member 24 functions to remove particulate which may be present in the fluid being filtered. Especially important is the removal of blood clots from whole blood. The filter screen member 24 is preferably made from nylon, and typically has openings in excess of 150 microns.

Located downstream from the filter screen member 24, and in fluid communication with the filter chamber 14, is the pump chamber 16. The pump chamber 16 is an elongated flexible member with a top opening 28 and a bottom opening 30. As fluid exits the filter screen member 24, it passes through the top opening 28 and enters the pump chamber 16. The bottom opening 30 of the pump chamber 16 allows fluid to exit the inlet blood filter unit 10. To facilitate the flow of fluid through the bottom opening 30, the pump chamber 16 may be compressed. Thus, the flow of fluid through the inlet blood filter unit 10 is from the spike 20 through the drop former 22 through the drip chamber 12, into the filter chamber 14, through the filter screen member 24, into the pump chamber 16 and through the bottom opening 30.

Located at the bottom opening 30 of the pump chamber 14 is an administration set tubing 32. The administration set tubing 32 may be bonded to the bottom opening 30 by solvent bonding or other type of bond. The administration set tubing 32 is then connected to an IV or other tubing so that fluid may be directed into a patient.

Because blood is usually stored in a cold environment, the flow of the blood through the inlet blood filter assembly 10 and into the administration set tubing 32 is usually slow. Thus, when blood is being administered to a trauma patient who has experienced a large loss of blood, it becomes necessary to increase the flow rate of the blood. The pump chamber 16 functions to increase the flow rate of the blood through the inlet filter assembly 10 by forcing the blood through the bottom opening 30 of the inlet blood filter assembly 10 and into the administration set tubing 32 and the patient.

In order to increase the flow rate, the pump chamber is compressed thereby forcing the blood into the administration set tubing 32. To prevent the blood from flowing upstream, i.e., into the filter chamber 14, a ball check 34 is used. When the pump chamber 16 is compressed, the ball check 34 seats against the top opening 28 of the pump chamber 16 preventing the flow of blood into the filter chamber 14. The ball check 34 is designed to perfectly seat at the top opening 28 of the pump chamber 16, thereby preventing the flow of any blood into the filter chamber 14. Because the pump chamber 16, when in use, is filled with fluid, the ball check 34 floats near the top opening 28 of the pump chamber 16. Thus, when the pump chamber 16 is compressed, the ball check 34 immediately seats at the top opening 28 of the pump chamber 16 preventing the reverse flow of blood. It should be noted, that the ball check 34 does not prevent the flow of blood into the pump chamber 16 as the force of gravity is sufficient to move the ball check 34 and prevent it from seating on the top opening 28 when the pump chamber 16 is not being compressed.

Because the pump chamber 16 is located downstream of the filter chamber 14, and more specifically the filter screen member 24, compression of the pump chamber 16 does not force fluid through the filter screen member 24. When fluid is forced through the filter screen member 24 the efficiency of the filter screen is reduced proportionately to the pressure exerted on the fluid. By locating the pump chamber 16 downstream of the filter chamber 14 the present invention provides an inlet blood filter assembly 10 with a pump chamber 16 which may be used to expedite the flow of blood into a patient without sacrificing the filter's efficiency. This is especially important when cold whole blood is being introduced into a patient as it is usually laden with blood clots.

The inlet blood filter assembly 10 is created through an injection blow molding process. Specifically, the inlet blood filter assembly 10 is created through open ended blow molding. This process allows the inlet blood filter assembly 10 to be blow molded without one of its ends being closed off. The open ended blow molding process is described in detail in U.S. Pat. No. 3,950,468, to which reference is now made. The preferred open ended blow molding process is utilized by Rainville Company, Inc., 200 Clay Avenue, Middlesex, N.J. 08846. Through the use of the injection blow molding process, one is able to vary the wall thickness of the drip, filter and pump chambers, thereby saving material and creating a more efficient pump chamber 16.

In a preferred embodiment, the inlet blood filter assembly 10 is blow molded so that the walls 36 of the pump chamber 16 are thinner than the walls 38 of the drip chamber 12 and as thin or thinner than the walls 40 of the filter chamber 14.

By varying the wall thickness of the chambers not only may a more efficient inlet blood filter assembly 10 be created but also a less expensive assembly because excess material is not used and wasted. By decreasing the wall 36 thickness of the pump chamber 16 a more usable inlet blood filter assembly 10 is created. This construction provides a pump chamber 16 which is easily compressed thereby lessening the chances that the inlet blood filter assembly 10 would accidentally be disengaged from the blood bag or IV during use. It has been found that a pump chamber 16 with a wall thickness of about 0.02 to 0.03 inches provides a very flexible yet sturdy chamber which is easily compressed.

Because the inlet blood filter assembly 10 of the present invention is created through injection blow molding, it may be an integral unit. Thus, the three chambers do not need to be bonded or crimped together but instead, are molded from a single tube of plastic. This not only decreases the time needed to create the inlet blood filter assembly units 10, but also creates an inlet blood filter assembly 10 which does not have joints or connections which may fail. Furthermore, because the joints are not crimped together but instead are blow molded, the ball-check will perfectly seat between the pump chamber 16 and filter chamber 14 when the pump chamber is compressed. This is especially important when the pump chamber 16 is located below the filter chamber 14.

It should also be understood that various changes and modifications to the preferred embodiments described herein will be apparent to those skilled in the art. Such changes and modifications can be made without departing from the spirit and scope of the present invention and without diminishing its attendant advantages. It is therefore, intended that such changes and modifications be covered by the following claims.

I claim:

1. An integral inlet blood filter assembly comprising:
   a drip chamber including wall members;
   a filter chamber including wall members; and
   a pump chamber, the pump chamber having wall members which are thinner than the drip chamber wall members and the drip, filter and pump chambers being so arranged and constructed that blood flows from the drip chamber into the filter chamber and then into the pump chamber;
   wherein the drip chamber wall members, filter chamber wall members, and pump chamber wall members are all formed from a single piece of thermoplastic material.

2. The apparatus of claim 1 wherein the wall members of the pump chamber are about 0.02 to 0.03 inches thick.

3. The apparatus of claim 1 wherein the wall members of the filter chamber are as thick as the wall members of the pump chamber.

4. The apparatus of claim 1 wherein the pump chamber includes a ball-check for preventing the reverse flow of blood from the pump chamber into the filter chamber when the pump chamber is compressed.

5. The apparatus of claim 4 including:
   a spike solvent bonded to an end of the drip chamber; and
   an administration set tubing solvent bonded to an end of the pump chamber.

6. The apparatus of claim 1 wherein the wall members of the filter chamber are as thick as the wall members of the drip chamber.

7. An inlet blood filter assembly comprising:
   a drip chamber including wall members;
   a filter chamber including wall members; and
   a pump chamber including wall members which are thinner and more flexible than the wall members of the drip chamber;
   said drip, filter and pump chambers being arranged so that blood flows from the drip chamber into the filter chamber and then into the pump chamber;
   said wall members of the drip, filter and pump chambers being formed of a single piece of material.

8. The appratus of claim 7 wherein the wall members of the pump chamber are about 0.02 to 0.03 inches thick.

9. The apparatus of claim 7 wherein the wall members of the filter chamber are as thick as the wall members of the pump chamber.

* * * * *